(12) United States Patent
Tamir

(10) Patent No.: US 10,828,150 B2
(45) Date of Patent: Nov. 10, 2020

(54) DOCKING STATION FOR HEART VALVE PROSTHESIS

(71) Applicant: Edwards Lifesciences Corporation, Irvine, CA (US)

(72) Inventor: Ilan Tamir, Hefzi-Bah (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/643,229

(22) Filed: Jul. 6, 2017

(65) Prior Publication Data

US 2018/0008404 A1    Jan. 11, 2018

Related U.S. Application Data

(60) Provisional application No. 62/360,160, filed on Jul. 8, 2016.

(51) Int. Cl.
*A61F 2/24* (2006.01)

(52) U.S. Cl.
CPC .......... *A61F 2/2409* (2013.01); *A61F 2/2418* (2013.01); *A61F 2230/0006* (2013.01); *A61F 2230/0013* (2013.01); *A61F 2230/0054* (2013.01); *A61F 2250/006* (2013.01); *A61F 2250/0037* (2013.01); *A61F 2250/0039* (2013.01)

(58) Field of Classification Search
None
See application file for complete search history.

(56) References Cited

U.S. PATENT DOCUMENTS

| | | | |
|---|---|---|---|
| 4,035,849 | A | 7/1977 | Angell et al. |
| 5,059,177 | A | 10/1991 | Towne et al. |
| 5,411,552 | A | 5/1995 | Andersen et al. |
| 5,554,185 | A | 9/1996 | Block et al. |
| 5,840,081 | A | 11/1998 | Andersen et al. |
| 6,168,614 | B1 | 1/2001 | Andersen et al. |
| 6,419,696 | B1 | 7/2002 | Ortiz et al. |
| 6,432,134 | B1 | 8/2002 | Anson et al. |
| 6,458,153 | B1 | 10/2002 | Bailey et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Leslie Lopez
(74) *Attorney, Agent, or Firm* — Guy Cumberbatch; Hans P. Smith

(57) ABSTRACT

An anchoring device that can be positioned within a native valve, such as the native mitral valve, to secure a replacement prosthetic valve in place. The anchoring device can comprise a docking station formed of a super elastic wire-like member defining a continuous, closed shape. The docking station can have an upper or atrial ring with at least two ring portions or half rings that are spaced apart across gaps. Descending bends from the ends of the two ring portions lead to a pair of anchors. The anchors can include oppositely-directed rounded V-shaped arms that extend generally parallel to the upper ring. When installed by a delivery device, the anchors can be located in the subvalvular space or the region/vicinity of the native leaflets and pinch the leaflets and the annulus against the upper ring which is located on the other side of the annulus.

19 Claims, 7 Drawing Sheets

(56) References Cited

U.S. PATENT DOCUMENTS

| | | |
|---|---|---|
| 6,527,979 B2 | 3/2003 | Constantz et al. |
| 6,582,462 B1 | 6/2003 | Andersen et al. |
| 6,652,578 B2 | 11/2003 | Bailey et al. |
| 6,730,121 B2 | 5/2004 | Ortiz et al. |
| 6,797,002 B2 | 9/2004 | Spence et al. |
| 6,908,481 B2 | 6/2005 | Cribier |
| 7,018,408 B2 | 3/2006 | Bailey et al. |
| 7,037,334 B1 | 5/2006 | Hlavka et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,585,321 B2 | 9/2009 | Cribier |
| 7,618,446 B2 | 11/2009 | Andersen et al. |
| 7,708,775 B2 | 5/2010 | Rowe et al. |
| 7,737,060 B2 | 6/2010 | Strickler et al. |
| 7,785,366 B2 | 8/2010 | Maurer et al. |
| 7,951,195 B2 | 5/2011 | Antonsson et al. |
| 8,236,049 B2 | 8/2012 | Rowe et al. |
| 8,323,335 B2 | 12/2012 | Rowe et al. |
| 8,377,115 B2 | 2/2013 | Thompson |
| 8,398,708 B2 | 3/2013 | Meiri et al. |
| 8,449,605 B2 | 5/2013 | Lichtenstein et al. |
| 8,449,606 B2 | 5/2013 | Eliasen et al. |
| 8,657,872 B2 | 2/2014 | Seguin |
| 8,663,322 B2 | 3/2014 | Keranen |
| 8,672,998 B2 | 3/2014 | Lichtenstein et al. |
| 8,685,086 B2 | 4/2014 | Navia et al. |
| 8,734,507 B2 | 5/2014 | Keranen |
| 9,078,747 B2 | 7/2015 | Conklin |
| 9,095,434 B2 | 8/2015 | Rowe |
| 9,119,718 B2 | 9/2015 | Keranen |
| 9,237,886 B2 | 1/2016 | Seguin et al. |
| 9,364,326 B2 | 6/2016 | Yaron |
| 9,463,268 B2 | 10/2016 | Spence |
| 9,474,599 B2 | 10/2016 | Keranen |
| 9,597,205 B2 | 3/2017 | Tuval |
| 9,622,863 B2 | 4/2017 | Karapetian et al. |
| 2002/0032481 A1 | 3/2002 | Gabbay |
| 2002/0107535 A1 | 8/2002 | Wei et al. |
| 2003/0225420 A1 | 12/2003 | Wardle |
| 2004/0111006 A1 | 6/2004 | Alferness et al. |
| 2004/0260389 A1 | 12/2004 | Case et al. |
| 2005/0010287 A1 * | 1/2005 | Macoviak .............. A61F 2/2445 623/2.36 |
| 2005/0096736 A1 | 5/2005 | Osse et al. |
| 2005/0119682 A1 | 6/2005 | Nguyen et al. |
| 2005/0119735 A1 | 6/2005 | Spence et al. |
| 2005/0137691 A1 | 6/2005 | Salahieh et al. |
| 2005/0182486 A1 | 8/2005 | Gabbay |
| 2005/0203614 A1 | 9/2005 | Forster et al. |
| 2005/0203617 A1 | 9/2005 | Forster et al. |
| 2006/0025857 A1 | 2/2006 | Bergheim et al. |
| 2007/0203575 A1 | 8/2007 | Forster et al. |
| 2007/0265700 A1 | 11/2007 | Eliasen et al. |
| 2007/0293808 A1 | 12/2007 | Williams et al. |
| 2008/0033542 A1 | 2/2008 | Antonsson et al. |
| 2008/0065204 A1 | 3/2008 | Macoviak et al. |
| 2008/0077235 A1 | 3/2008 | Kirson |
| 2008/0125853 A1 | 5/2008 | Bailey et al. |
| 2008/0208330 A1 | 8/2008 | Keranen |
| 2009/0319037 A1 | 12/2009 | Rowe et al. |
| 2010/0145440 A1 | 6/2010 | Keranen |
| 2010/0312333 A1 | 12/2010 | Navia et al. |
| 2010/0318184 A1 | 12/2010 | Spence |
| 2012/0059458 A1 | 3/2012 | Buchbinder et al. |
| 2012/0283820 A1 | 11/2012 | Tseng et al. |
| 2013/0006352 A1 | 1/2013 | Yaron |
| 2013/0304197 A1 | 11/2013 | Buchbinder et al. |
| 2014/0172070 A1 | 6/2014 | Seguin |
| 2014/0358222 A1 | 12/2014 | Gorman, III et al. |
| 2014/0379074 A1 | 12/2014 | Spence et al. |
| 2015/0230921 A1 | 8/2015 | Chau et al. |
| 2015/0245910 A1 | 9/2015 | Righini et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |
| 2015/0374493 A1 | 12/2015 | Yaron et al. |
| 2016/0074165 A1 | 3/2016 | Spence et al. |
| 2016/0095705 A1 | 4/2016 | Keranen et al. |
| 2016/0184095 A1 | 6/2016 | Spence et al. |
| 2016/0199177 A1 | 7/2016 | Spence et al. |
| 2016/0256276 A1 | 9/2016 | Yaron |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0217385 A1 | 8/2017 | Rinkleff et al. |
| 2017/0266005 A1 | 9/2017 | McGuckin, Jr. |
| 2017/0273788 A1 | 9/2017 | O'Carroll et al. |
| 2018/0206074 A1 | 7/2018 | Tanasa et al. |

FOREIGN PATENT DOCUMENTS

| | | |
|---|---|---|
| EP | 0592410 B1 | 10/1995 |
| EP | 0850607 A1 | 7/1998 |
| EP | 1296618 B1 | 1/2008 |
| EP | 1827314 B1 | 12/2010 |
| EP | 2620125 A1 | 7/2013 |
| EP | 2806829 A2 | 12/2014 |
| NO | 2016038017 | 3/2016 |
| WO | 1991017720 A1 | 11/1991 |
| WO | 01/49213 A2 | 7/2001 |
| WO | 01/54625 A1 | 8/2001 |
| WO | 02/47575 A2 | 6/2002 |
| WO | 2005084595 A1 | 9/2005 |
| WO | 2005102015 A2 | 11/2005 |
| WO | 2006011127 A2 | 2/2006 |
| WO | 2007067942 A1 | 6/2007 |
| WO | 2009155561 A2 | 12/2009 |
| WO | 2010121076 A2 | 10/2010 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015118464 A1 | 8/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |

* cited by examiner

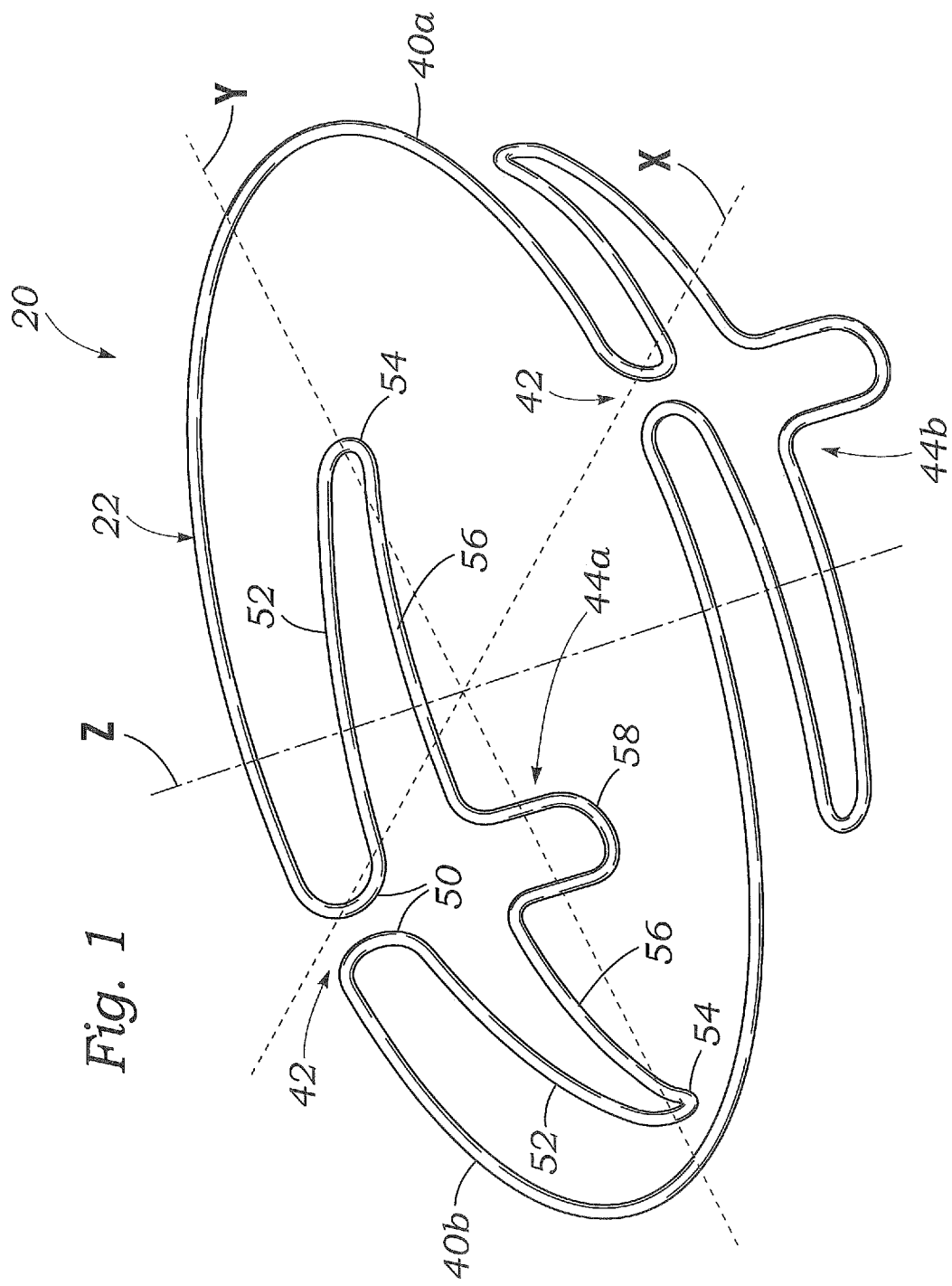

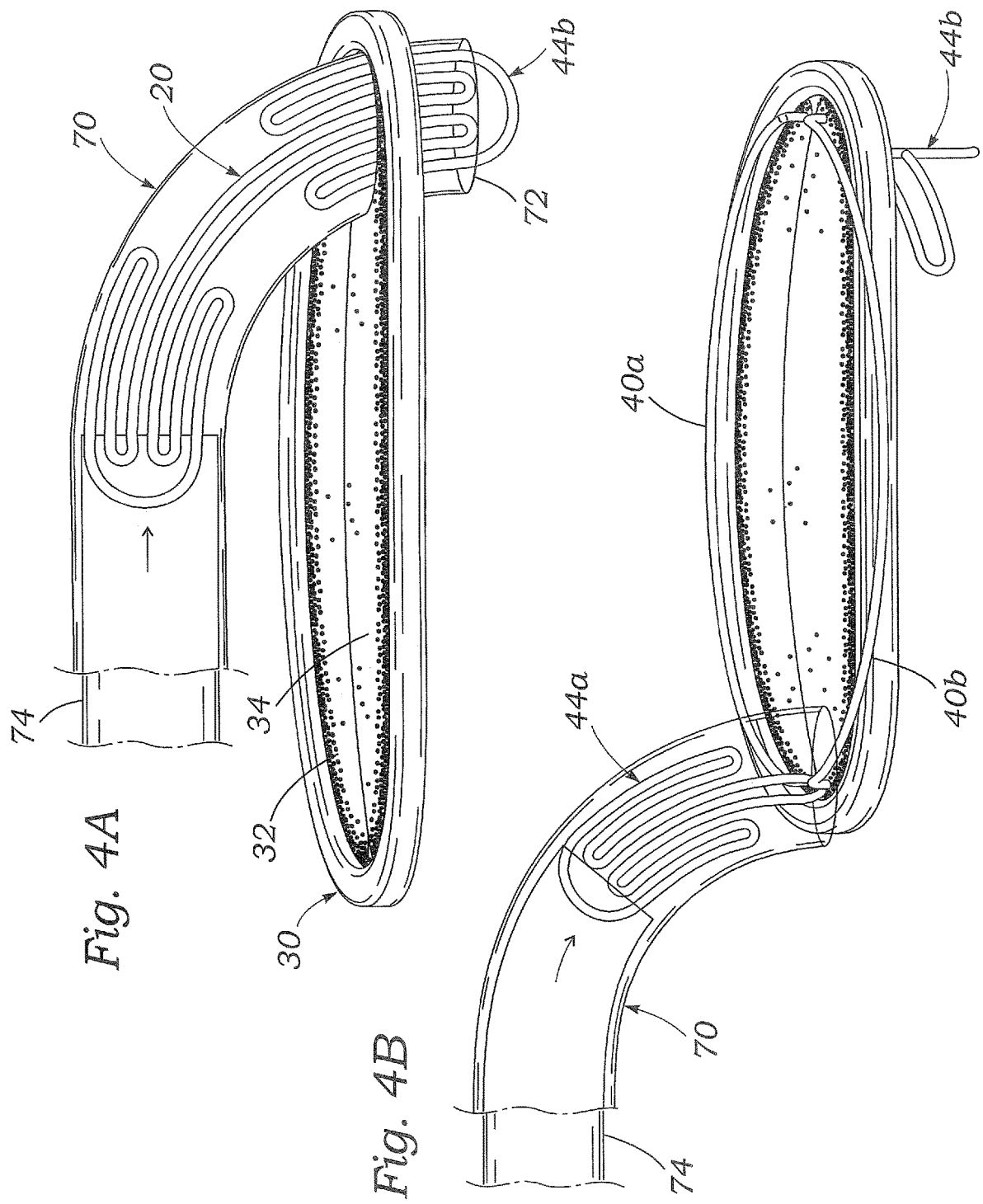

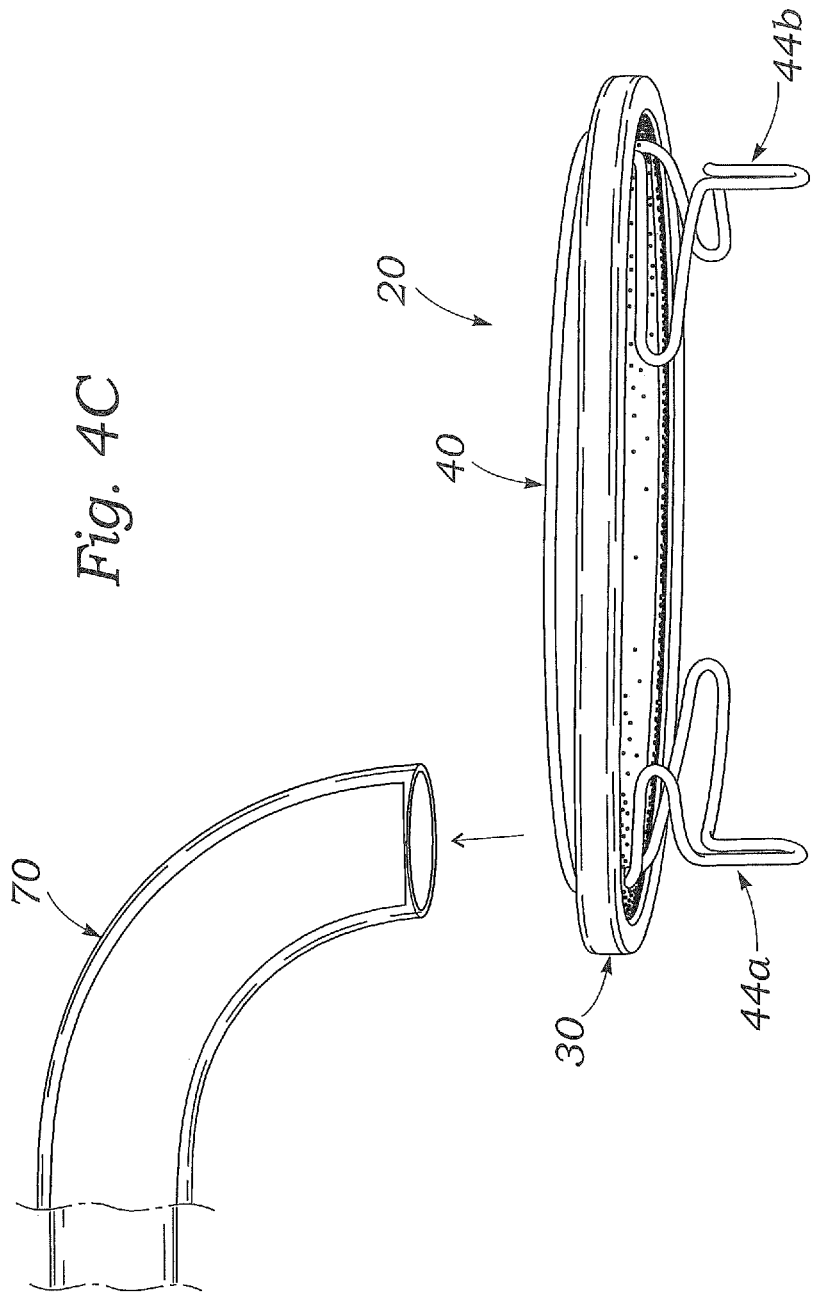

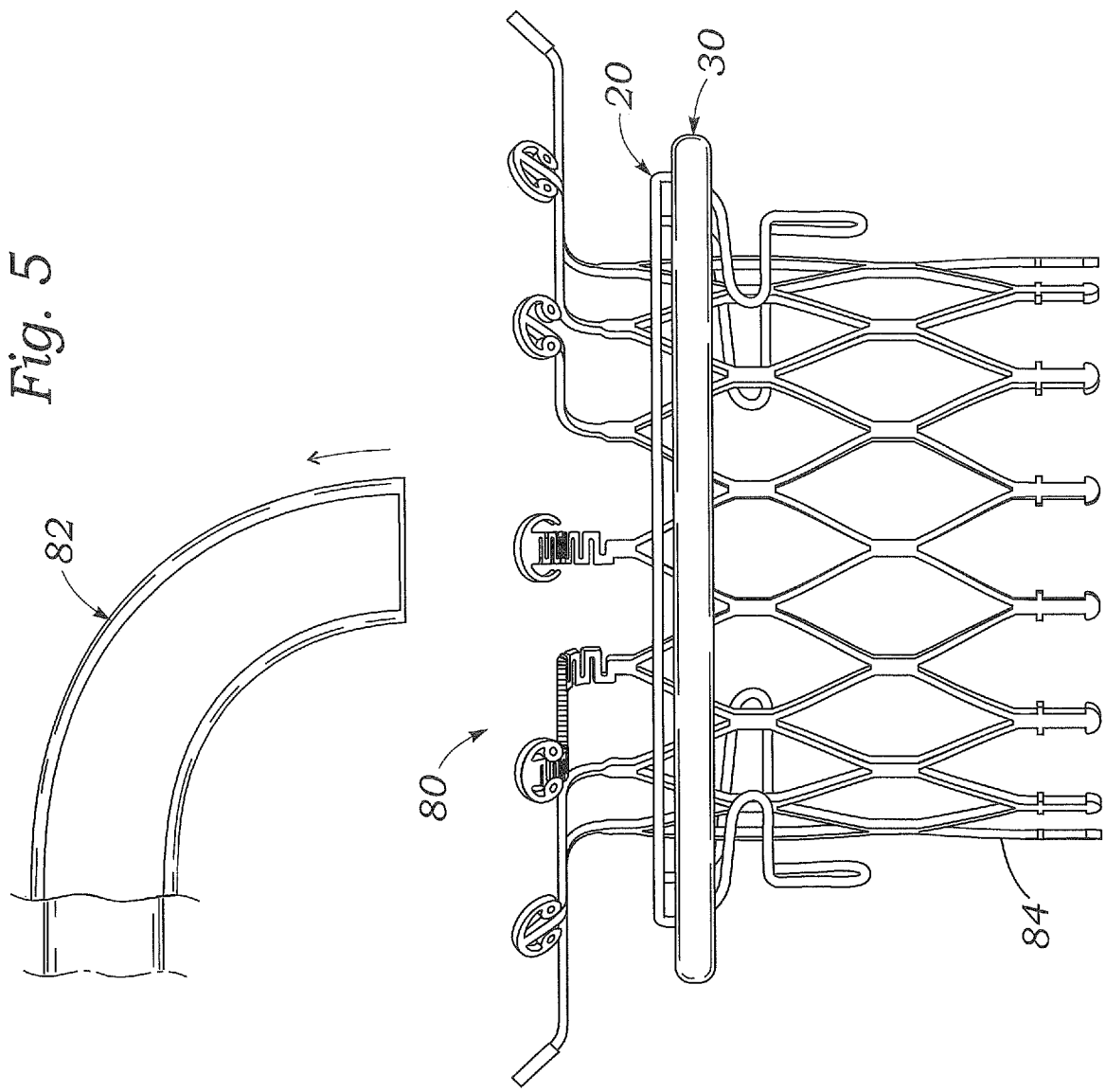

DOCKING STATION FOR HEART VALVE PROSTHESIS

RELATED APPLICATIONS

The present application claims priority under 35 U.S.C. § 119 to U.S. Provisional Ser. No. 62/360,160, filed Jul. 8, 2016, which is incorporated by reference herein in its entirety.

FIELD OF THE INVENTION

The present invention relates to anchoring devices that can be positioned within a native valve for securement of a replacement valve.

BACKGROUND OF THE INVENTION

Mitral valve regurgitation occurs when blood flows back through the mitral valve and into the left atrium when the ventricle contracts. Heart valve regurgitation can occur when the heart leaflets do not completely close when the heart contracts. For example, when the heart contracts, blood flows back through the improperly closed leaflets.

In some instances regurgitation occurs due to disease of the valve leaflets (e.g., primary, or "organic" regurgitation). Regurgitation can also be cause by dilatation of the left ventricle, which can lead to secondary dilatation of the mitral valve annulus. Dilation of the annulus spreads the mitral valve leaflets apart and creates poor tip cooptation and secondary leakage, or so-called "functional regurgitation."

Primary regurgitation can be corrected by attempting to remodel the native leaflets, such as with clips, sutures, hooks, etc., to allow them to close completely when the heart contracts. When the disease is too far advanced, the entire valve may need to be replaced with a prosthesis, e.g., mechanical or biologic. Based on the success of catheter-based aortic valve replacement, it would be beneficial to have options usable to replace the mitral valve non-invasively using similar types of replacement valves.

Unlike the aortic valve, however, the mitral valve annulus does not provide a good landmark for positioning a replacement mitral valve. The bulk of the aortic annulus is generally increased in the presence of degenerative disease associated with calcium formation, thus making it easier to properly secure a replacement aortic valve in place due to the reduced cross-sectional area of the aortic annulus. However, in mitral valves experiencing regurgitation, the mitral valve annulus is generally thinner not thicker, wider not narrower. The thinner, wider mitral valve annulus makes it relatively more difficult to properly seat a replacement mitral valve in the native mitral valve annulus. Further, the aortic annulus is anatomically pronounced, providing a larger "bump" to which a replacement aortic valve can be secured, whereas the smoother transition from the left atrium to the left ventricle defined by the mitral valve annulus makes it more difficult to properly anchor a replacement mitral valve in place.

Further, the larger mitral valve annulus makes it difficult to securely implant current percutaneously delivered valves in the native mitral position. Current replacement aortic valves are limited in the amount of radial expansion they can undergo during deployment and implantation. To provide a replacement aortic valve that has an expanded configuration such that it can be securely anchored in a mitral valve annulus would require that the collapsed delivery profile of the replacement aortic valve be increased. However, that would make endovascular delivery more dangerous for the patient and more difficult to navigate the vasculature with a larger diameter delivery system. Further, self-expanding stents that cause the valve to become anchored to the valve annulus may not be feasible for repair of a mitral valve due to the possibility that the self-expanding stent may occlude the left ventricle outflow tract for the adjacent aortic valve.

Some attempts have been made to first deliver and implant an anchor to the mitral valve and then a prosthetic valve into the anchor. For instance, U.S. Pat. No. 8,657,872 to Seguin and U.S. Pat. No. 9,301,836 to Buchbinder disclose such systems, and these references are incorporated by reference herein in their entirety. However, these devices have not caught on with surgeons for a variety of reasons.

Despite certain advances in mitral valve replacement, there remains a need for new effective and safe anchoring devices that can be positioned near or within the native mitral valve and that is adapted to secure a replacement mitral valve in place.

SUMMARY OF THE INVENTION

This summary is meant to provide some examples and is not intended to be limiting of the scope of the invention in any way. For example, any feature included in an example of this summary is not required by the claims, unless the claims explicitly recite the features. Various features and steps as described elsewhere in this disclosure may be included in the examples summarized here, and the features and steps described here and elsewhere can be combined in a variety of ways.

The present application discloses a docking station meant to support, when implanted in a native valve, any kind of expandable prosthetic valve (e.g., self-expandable/balloon-expandable/mechanical/hydraulic/combination, etc.). The docking station is configured such that it does not significantly interfere with the native leaflets (e.g., the native mitral leaflets) after it is installed so it allows sufficient performance of the native valve during the time it takes to subsequently put in the prosthetic valve. When implanted in a native mitral valve, the docking station is configured to support the anterior mitral leaflet from its back side to prevent it from compromising flow through the left ventricular outflow tract (LVOT) or aorta during systole. The docking station is low profile and can be delivered through the femoral or radial vein in a trans-septal procedure.

A number of distinct benefits are provided by the docking station disclosed herein. First of all, the docking station has a very small profile to reduce the size of any delivery devices used for installation. Secondly, the placement and installation of the docking station is relatively simple and can be done with reduced imaging requirements, e.g., using left atrial imaging only. The docking station is configured to sit high in the native annulus (e.g., in a native mitral annulus), which allows for the installation of a larger prosthetic mitral valve. Also, there is no need to loop around chordae tendineae, as with some prior devices. The single piece docking station installs independently in the native annulus without any sutures or other such fasteners. The docking station is universal in that it may receive all kinds of prosthetic valves (e.g., self-expandable/balloon-expandable/mechanical/hydraulic/combination, etc.). Furthermore, when implanted in a native mitral valve, the docking station prevents LVOT or aorta obstruction by the native anterior leaflet or by deformation of the annulus and/or aorta due pressure from an anchor, docking station, prosthetic valve, etc. Finally, the docking station permits continuing performance of the native leaflets after its installation so that no significant valve regurgitation (e.g., mitral regurgitation (MR)) is created during the period of time between the docking station placement and the prosthetic valve placement.

In one embodiment, a heart valve docking station (e.g., mitral heart valve docking station) comprises a super elastic wire-like member (e.g., a wire-like elongated member) forming a continuous, closed shape. The shape defines a first ring (e.g., an upper ring, an atrial ring, etc.) arranged around a central axis and sized to circumscribe a native annulus (e.g., a mitral annulus) including at least two ring portions (e.g., two half rings, such as a first half ring and a second half ring; three portions or three ⅓ ring portions; and so on) lying in a horizontal plane, the at least two portions (e.g., two half rings, etc.) being separated at two pairs of adjacent ends by gaps. A symmetric pair of descending bends on both pairs of adjacent ends of the at least two portions (e.g., two half rings, etc.) extend vertically downward from the adjacent ends and turning through an included angle of approximately 180°. A pair of generally V-shaped arcuate arms (e.g., V-shaped ventricular arms) extend from each pair of descending bends below the horizontal plane of the first ring (e.g., the upper ring or atrial ring) with apices pointed away from each other, and a lower strut on each arm (e.g., each ventricular arm) of each pair connects to the lower strut on the other arm (e.g., the other ventricular arm) of that pair.

The native heart valve docking station (e.g., native mitral valve docking station) can comprise a wire-like member (e.g., a wire-like elongated member) defining at least two portions (e.g., two half rings, three portions or three ⅓ ring portions, etc.) arranged around a central axis and separated at pairs of adjacent ends by gaps, the at least two portions (e.g., two half rings, etc.) defining an incomplete ring sized to fit around a native valve annulus (e.g., a mitral annulus). A pair of anchors (e.g., ventricular anchors) can be included and can each connect to a pair of adjacent ends of the ring portions (e.g., of the half rings) and be axially spaced from the ring portions (e.g., from the half rings). Each of the anchors (e.g., ventricular anchors) can have two arms (or another number of arms, e.g., 1, 3, 4, 5, 6 or more) extending away from each other, and each anchor (e.g., ventricular anchor) can be curved generally around the central axis and spaced radially inward from the ring portions (e.g., from the half rings).

The first ring (e.g., the upper ring or atrial ring) of any of the docking stations herein can form a circle interrupted by the gaps, such as, for example, an angular span of each ring portion (e.g., each half ring) being between 170-178° and the gaps can have a preferred width of between 1-6 mm. The arms (e.g., ventricular arms) can each be curved generally around the central axis, and each can have a radius of curvature less than a radius of the first ring (e.g., the upper ring or atrial ring). For instance, a diameter of the first ring (e.g., the upper ring or atrial ring) can be between about 25-33 mm, while the arms (e.g., ventricular arms) have a radius of curvature that is about 2-3 mm less than the radius of the first ring (e.g., the upper ring or atrial ring). The arms (e.g., ventricular arms) can each descend down below the horizontal plane of the first/upper ring (e.g., of the atrial ring) to a preferred depth of between about 10-15 mm. Though some exemplary measurements and ranges are listed herein, it should be understood that other measurements/ranges are also possible.

In any of the docking stations, the arms of each anchor (e.g., ventricular anchor) can have a rounded V-shape formed by an upper strut, a curved end defining an apex of the arm, and a lower strut, and the lower strut of each pair of arms can, optionally, connect to the lower strut on the other arm of that pair. Optionally, the lower strut on each arm (e.g., ventricular arm) of each pair can connect to the lower strut on the other arm (e.g., ventricular arm) of that pair via a downwardly curved bridge portion that extends downward from the lower struts. The member/elongated member can be formed from a single length of wire having two free ends connected by a crimp or, optionally, the member/elongated member can be formed by laser cutting the continuous form from a metallic tube such as a Nitinol tube.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIG. 1 is a perspective view of an exemplary valve docking station of the present application, while

FIGS. 4A-4C illustrate several steps in an exemplary procedure for installing the docking station at a native annulus (e.g., mitral annulus) using a delivery tube/catheter;

FIG. 5 illustrates an exemplary prosthetic expandable heart valve implanted by a delivery device at the native annulus (e.g., mitral annulus) in which the docking station has been installed.

DETAILED DESCRIPTION OF PREFERRED EMBODIMENTS

FIG. 1 is a perspective view of an exemplary valve docking station 20 of the present application that can be used in a native valve of a heart (e.g., in a mitral valve, tricuspid valve, aortic valve, pulmonary valve). While the docking station may be described, for example, as a mitral valve docking station and may be described and shown as being used, for example, in a native mitral valve, it should be understood that the docking station and concepts herein are representative and can be adapted for use in other valves. The docking station 20 illustrated in FIG. 1 comprises a super elastic (e.g., Nitinol) solid member or elongated member 22 that may be cut from a tube or be bent out of a wire. Indeed, the docking station 20 can comprise a continuous length of rod or wire, preferably circular in cross-section, which is highly flexible throughout, however, one or more non-continuous length(s) of rod or wire could also be used and could have one or more of a variety of cross-sectional shapes, e.g., oval, ovoid, square, rectangular, hexagonal, triangular, etc. Preferably, the member or elongated member 22 is a single length of round wire that is shaped (bent and possibly heat set) to the geometry described below and then its ends are welded or crimped together to form a closed "ring." (A weld or crimp will preferably be located in a region of low elastic stress.) But a variety of arrangements and constructions are possible. Optionally, the docking station 20 can be made out of laser cut nitinol tube or cone.

In this case the docking station 20 will comprises the same features ("springy" atrial ring and ventricular arms, as described) but the geometry will likely be changed to enable crimping of the rectangular cross section of the wire. The rectangular cross section may be smoothed somewhat with electropolishing or the like.

For the purpose of orientation, the docking station 20 has a shape that can be defined relative to an X-Y-Z coordinate system as shown in FIG. 1. As will be explained, when installed the vertical or Z-axis corresponds to an approximate direction of flow through the valve annulus (e.g., a mitral valve annulus). The horizontal or X/Y plane corresponds to the "plane" of the annulus. While the mitral annulus is very rarely planar, and often has a saddle shape with an upward bow on two sides, the high flexibility of the wire-like docking station 20 permits it to conform to an irregular annulus. As stated elsewhere, a super-elastic wire-like member/elongated member 22 of between 0.5-1.0 mm is preferred, but other sizes are possible larger or smaller than this.

Figure 2:
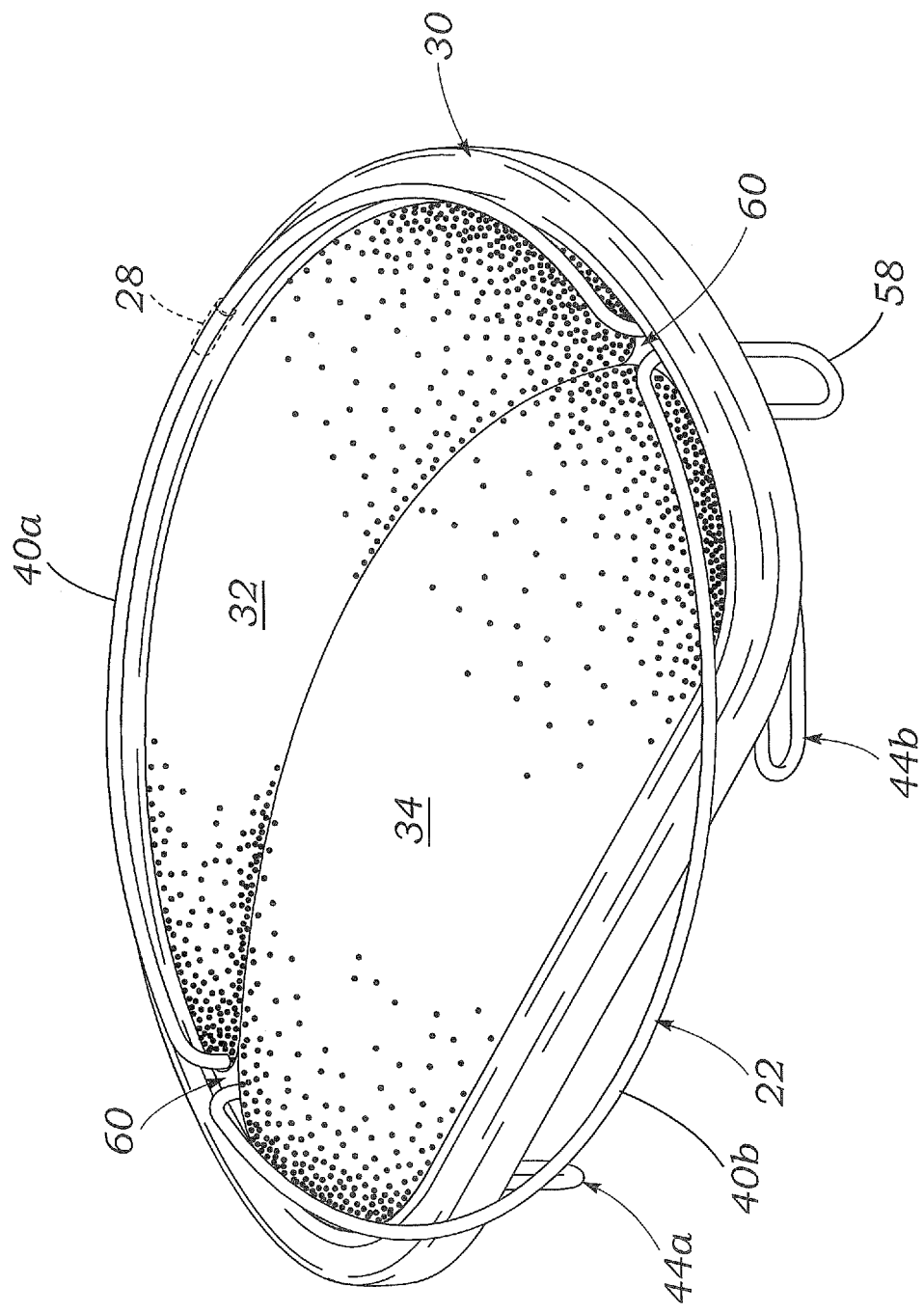
FIG. 2 is a perspective view of the docking station of FIG. 1 installed at a mitral annulus, shown schematically.

Prior to a detailed description of the shape of the docking station 20, the reader will note FIG. 2 which is a perspective view of the docking station installed at a mitral annulus 30, shown schematically. The mitral annulus 30 is illustrated as a tissue ledge having a continuous somewhat D-shaped profile looking down from above (e.g., FIG. 3A). A pair of flexible leaflets, namely a posterior leaflet 32 and an anterior leaflet 34 are shown extending inward toward each other from the peripheral annulus 30. The annulus 30 and leaflets 32, 34 are shown relatively smooth and idealized, and of course a natural mitral valve is often highly irregular; for instance, the leaflets are often broken into several scallops. Furthermore, the mitral valve exists between the right atrium and the left ventricle, and the tissue surrounding the mitral valve is not shown either. Finally, as will be described with respect to FIGS. 3B and 3C, the mitral annulus 30 is illustrated as being planar, but as mentioned above is often saddle shaped. The schematic illustration of the mitral valve herein should not be considered true for all anatomies, but the overall shape and position of the annulus and leaflets as shown is a good representative approximation.

With reference back to FIG. 1, the docking station 20 has a first/upper side (e.g., an atrial side) and a second/lower side (e.g., ventricular side). When implanted at a mitral valve annulus, up or along the positive Z-axis is towards the left atrium and down or along the negative Z-axis is toward the left ventricle. When implanted, the direction of blood flow through the docking station 20 is down or from the first/upper side to the second/lower side.

Figure 1A:
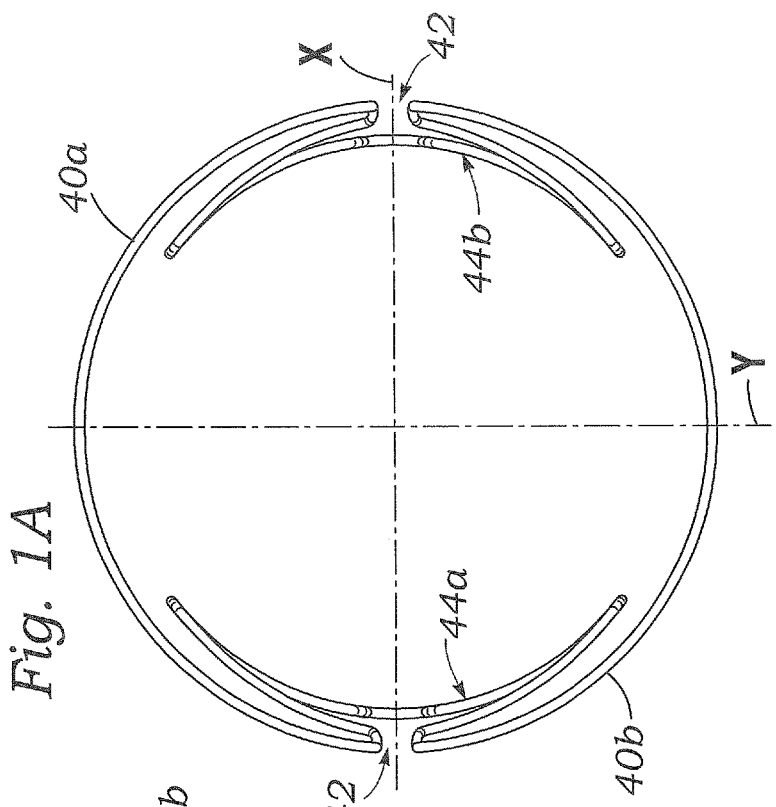
FIG. 1A is a top plan view thereof.

With reference back to FIG. 1 and the top plan view of FIG. 1A, the docking station 20 shown is particularly well adapted/configured for use in a mitral valve annulus and will be discussed below in terms of use in a mitral valve annulus, but the docking station can also be used in other native valves and can be modified/configured for those other valve, e.g., with three anchors instead of two, adjusted spacing, etc. The docking station 20 is shown to be symmetric about the X/Z plane, and comprises on its first/upper side (e.g., atrial side) a nearly complete circular or oval ring 40 formed of two ring sections/halves 40a, 40b. As seen in the top plan view of FIG. 1A, the ring halves 40a, 40b preferably lie in the X/Y plane and circumscribe an annular span of nearly 180° (e.g., 170-179°) each. The ends of each of the ring halves 40a, 40b are spaced apart from each other across opposed gaps 42 aligned along the X-axis. The gaps 42 are relatively small, e.g., 2-10°, such that the angular span of each ring half 40a, 40b is between 170-178° (atrial ring 40 diameter between 340-356°). In absolute terms, the gaps 42 may be between 1-6 mm. The rest of the member/wire 22 (e.g., elongated member) bends down to define two anchors 44a, 44b (e.g., ventricular anchors on the ventricular side of the X/Y plane or ventricular side of the mitral valve annulus) whose shape will be described below. The basic shape of the upper ring 40 is round or oval on the first/upper side or atrial side and the fingers-like design on the second/lower side or ventricular side provides compression without entangling with the chordae tendineae. An exemplary weld or crimp 28 is shown in dashed line in FIG. 2 at a midpoint of the ring half 40a which is a point of low stress, but may be located at other places on the member/elongated member 22 or in multiple places. Optionally, additional anchors can be used, e.g., three or four anchors instead of the two anchors 44a and 44b shown and spaced evenly apart or around the circumference, and the docking station can have similar gaps to those discussed above. The anchors can be of a similar design and shape to the anchors shown herein, but would be smaller if extra anchors are used.

From the four ends of the ring sections/halves 40a, 40b (or of more than two ring sections, if more than two anchors are used), the member/wire 22 (e.g., elongated member/wire) forms approximately 180° descending bends 50 leading to diverging upper or primary struts 52. Stated another way, a symmetric pair of descending bends 50 on both pairs of adjacent ends of the two ring sections/halves 40a, 40b extend vertically downward from the adjacent ends and turn through an included angle of approximately 180°. The primary struts 52 extend from the bends 50 generally parallel to and below the adjacent portions of the ring halves 40a, 40b, and each extend around a circumferential span of approximately 45°. The struts 52 then transition into curved ends 54 that lead to lower or secondary struts 56. The curved ends 54 also turn through an included angle of approximately 180° such that the secondary struts 56 on both anchors 44a, 44b (e.g., ventricular anchors) converge toward each other. The secondary struts 56 can be separated by a short downwardly curved bridge portion 58 which completes the continuity of the member/elongated member 22. The curved bridge portion 58 can help with crimping of the docking station 20 by relieving some resistance to bending at that location.

Figure 3A:
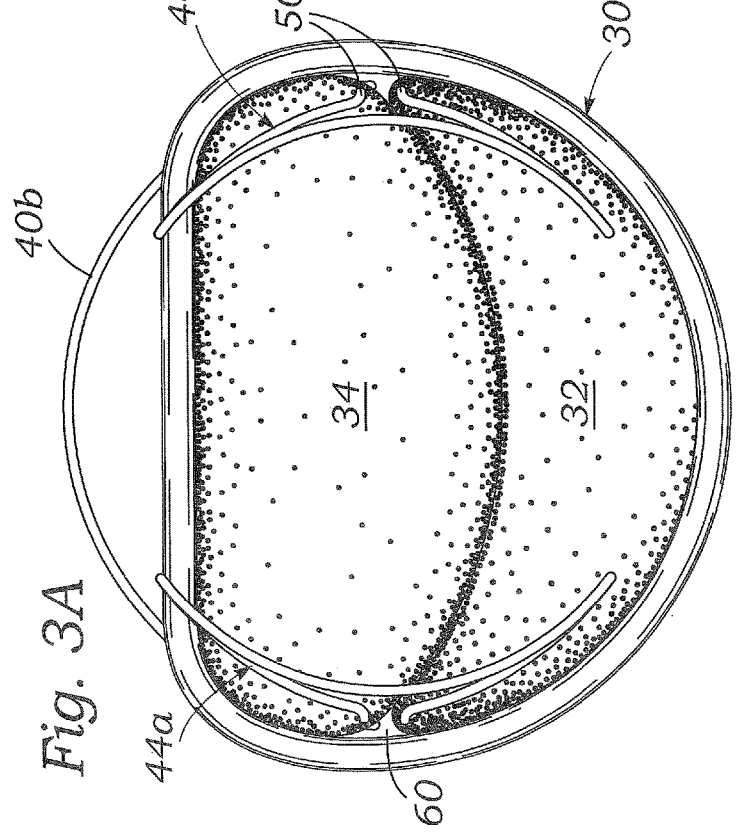
FIGS. 3A-3C are top plan, front elevational, and side elevational views, respectively, of the docking station installed at the mitral annulus.
Figure 3C:
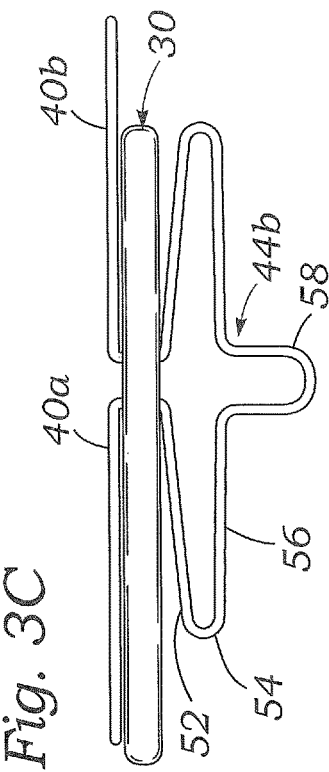

As best seen in FIGS. 1 and 3C, each of the anchors 44a, 44b (e.g., ventricular anchors) can form something of a T-shape with the bridge portion 58 defining the vertical leg of the T. In the Figures, each of the anchors 44a, 44b defines oppositely directed and symmetric posterior and anterior arcuate arms (e.g., ventricular arms); wherein the arms are made up of the generally rounded V-shaped projection formed by a primary strut 52, a curved end 54, and secondary strut 56. V-shaped as used herein encompasses U-shaped and similar shapes. Both arms of each anchor (e.g., of the anchors 44a and 44b and any additional anchors used) curve within and generally concentric to the upper atrial ring 40 and are located slightly radially inward therefrom. Because these arms commence at the line of symmetry in the X/Z plane, which as will be explained corresponds to the point at which the two leaflets 32, 34 of a mitral valve come together, they project away from one another to the posterior and anterior sides of the subvalvular structure below the mitral valve. The curved ends 54 each form an apex of the respective V-shaped arm (e.g., ventricular arm) that points away from the apex of the symmetrically opposed arm (e.g., ventricular arm).

Now again with reference to FIG. 2, the docking station 20 is shown installed at the mitral valve with the upper ring made up of the two ring halves 40*a*, 40*b* (anterior and posterior, respectively) extending around the mitral annulus 30 on the atrial side of the leaflets 32, 34. The two anchors 44*a*, 44*b* are shown as ventricular anchors that lie below the mitral annulus 30 on the ventricular side and extend under both posterior and anterior leaflets 32, 34. The 180° descending bends 50 extend down through commissure regions 60 of the mitral valve that are formed adjacent the mitral annulus 30 at the junction between the two leaflets 32, 34. Because of the T-shape of the ventricular anchors 44*a*, 44*b*, they diverge outward underneath the leaflets 32, 34. The leaflets 32, 34 are shown in coapting contact with one another corresponding to a valve closed configuration during systole, or when the left ventricle contracts and forces blood through the adjacent aortic valve. The anterior ventricular arms on both the ventricular anchors 44*a*, 44*b* extend under and prevent the anterior leaflet 34 from "inflating" or billowing, a condition that may compromise the left ventricular outflow tract (LVOT) during systole.

Figure 3B:
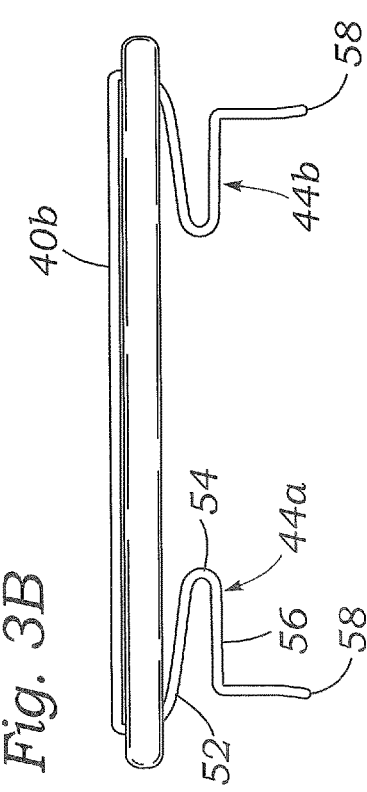

FIGS. 3A-3C further illustrate the positioning of the upper ring 40 and lower ventricular anchors 44 relative to the mitral annulus 30 and the leaflets 32, 34. The 180° descending bends 50 are seen passing between the leaflets 32, 34 at the commissures 60. FIG. 3A shows that the anchors/ventricular anchors 44 are positioned slightly radially inward from the upper ring 40. In a preferred embodiment, the anchors/ventricular anchors 44 are generally aligned along a circle (or oval) having a diameter (or major and minor dimensions) that is approximately 80-90% of the diameter (or major and minor dimensions) of the upper ring 40. The anchors/ventricular anchors 44 can press against the "ceiling" of the left ventricle so as to pinch the leaflets 32, 34 and a portion of the annulus 30 against the upper ring 40.

FIGS. 4A-4C illustrate several steps in a procedure for installing the docking station 20 at a native annulus 30 (illustrated for example as a mitral annulus) using a delivery tube 70. Initially, the delivery tube 70 is inserted into the body and advanced via vasculature (e.g., via the femoral or radial vein) to a desired location/portion of the heart (e.g., initially to the right atrium when installing in a mitral annulus). If initially advanced to the right atrium and access to the mitral annulus is desired, an access port can then be formed in the septal wall between the right atrium and the left atrium. A variety of ways of forming such an access port are known in the art, and will not be described further herein. The delivery tube 70 can then be advanced in a transseptal procedure across the septal wall and into the left atrium, above the mitral annulus 30.

A distal end 72 of the delivery tube 70 can be guided or steered between leaflets of a native valve (e.g., to a subvalvular position) and/or be positioned at a commissure of a native valve. For example, FIG. 4A shows a distal end 72 of the delivery tube 70 having been guided or steered between the mitral leaflets 32, 34 to a subvalvular position. The distal end 72 is positioned at one of the mitral valve commissures 60. Once properly positioned, the operator/health care provider/physician advances a pusher such as shown schematically at 74 through the delivery tube 70 to urge the docking station 20 distally such that it is partially expelled from the delivery tube. FIG. 4A illustrates the configuration of the docking station 20 when compressed within the delivery tube 70 such that the upper ring 40 is collapsed about its line of symmetry and one of the anchors/ventricular anchors 44*b* is positioned distal to the other anchor/ventricular anchor 44*a*.

The distal most anchor/ventricular anchor 44*b* is then expelled from the delivery tube 70 on a first side of the native annulus 30 (e.g., below the level of the mitral annulus), and expands into position as seen in FIG. 4B. The operator/health care provider/physician can then gradually expel the middle portion of the docking station 20, comprising the upper ring halves 40*a*, 40*b*, on a second side of the native annulus 30 (e.g., on the atrial side of the mitral annulus 30). After deployment of the upper ring 40, the docking station 20 is in the position of FIG. 4B.

Finally, the distal end 72 of the delivery tube 70 can be advanced between the leaflets (e.g., between leaflets 32, 34 into a subvalvular position), and the pusher 74 can be used to expel the proximal anchor/ventricular anchor 44*a* (not shown). Ultimately, the proximal anchor/ventricular anchor 44*a* expands below the native annulus 30 (e.g., below the mitral annulus) and into the position shown in FIG. 4C. The delivery tube 70 is retracted, as shown, and the docking station 20 is fully installed. Because the docking station 20 circumscribes the native leaflets (e.g., circumscribes the mitral leaflets 32, 34), and passes between them at the commissures 60 (see FIG. 3A), it does not interfere with their functioning after being installed. Of course, a reason for implanting the docking station 20 is for use as an anchor for a subsequently implanted prosthetic heart valve, and thus a minimum amount of time preferably elapses after installation of the docking station and before the new valve is implanted.

FIG. 5 illustrates an exemplary prosthetic expandable heart valve 80 having just been implanted by a delivery device 82 at the mitral annulus in which the docking station 20 has previously been installed. The heart valve 80 is shown schematically with just an expandable frame 84 as a representation of an exemplary prosthetic heart valve. Nonetheless, expandable heart valves usable with the docking stations herein can, for example, comprise an expandable frame, a cloth covering, and a plurality of bioprosthetic leaflets attached thereto. There are numerous types of expandable prosthetic heart valves that would benefit from anchoring within the docking station 20, including those made by Edwards Lifesciences of Irvine, Calif., Medtronic of Minneapolis, Minn., and St. Jude of Minneapolis, Minn.

The shape of the docking station 20 provides substantial elasticity along with spring stiffness for anchoring, thus it may also support prosthetic valves that get expanded to a particular diameter or to a fixed diameter (such as balloon expandable valves). A radial force induced between the docking station and the prosthetic valve can be sufficient to anchor an expandable prosthetic valve 80 inside the docking station 20. This force leverages the friction between the two (one expanding while the other contracting) to fix the prosthetic valve in place relative to the docking station 20, and since the native anatomy (e.g., leaflets) is pinched in between—the assembly is also fixed relative to the native anatomy. In order to generate this radial force, the ring/atrial ring 40 of the docking station 20 can expand and act like a spring. If the ring/atrial ring 40 was a simple Nitinol closed ring, it would require very high forces to expand (due to the stress vs strain properties of the nitinol), the fact that the first/upper portion or ring (e.g., the atrial member) here is made up of multiple ring portions or two half rings 40*a*, 40*b* with two openings 42 reduces the radial forces because these openings can be widened from expansion of the prosthetic valve. This allows the designer to control the radial force by changing the geometry of the atrial area of the ring. Further, the descending anchors/ventricular anchors 44*a*, 44*b* also contract inward against the prosthetic valve 80 and provide additional holding forces. Due to the axial dimension and curved shape, the anchors/ventricular anchors 44*a*, 44*b* provide a uniform holding force against a generally cylindrical outer frame of the prosthetic valve 80. Finally, as seen in FIG. 1A and described below, the anchors/ventricular anchors 44*a*, 44*b* can be angled radially inward from the atrial ring 40 a small amount to enhance this frictional anchoring effect.

Figure 6A:
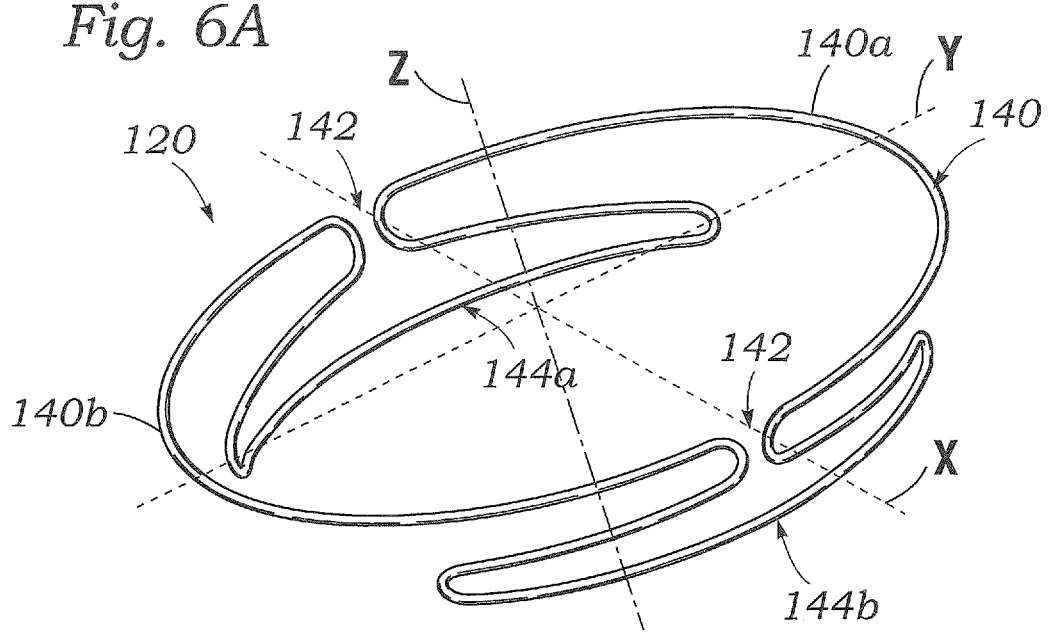
FIGS. 6A-6C illustrate an exemplary valve docking station of the present application.
Figure 6B:
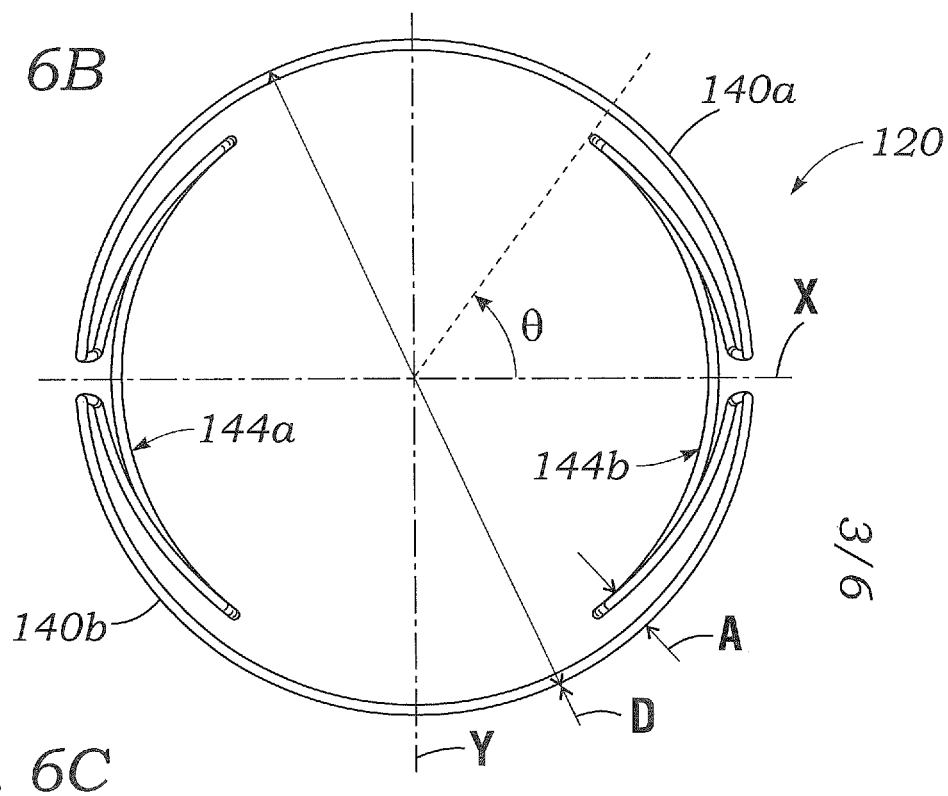
Figure 6C:
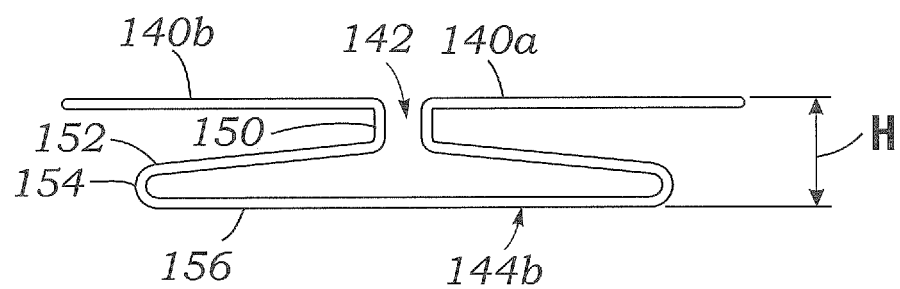

FIGS. 6A-6C illustrate another exemplary valve docking station 120 of the present application. As above, the docking station 120 is symmetric about the X/Z plane, and comprises on its first/upper side (e.g., atrial side) a nearly complete circular or oval ring 140 formed of two ring portions/halves 140*a*, 140*b*, though other shapes and numbers of ring portions (e.g., 3 ring portions or more) are also possible. The ring portions (e.g., ring portions/halves 140*a*, 140*b*) preferably lie in the X/Y plane and together circumscribe nearly a full 360° (e.g., if two are used, then ring portions/halves 140*a*, 140*b* can circumscribe an annular span of nearly 180° each). The ends of each of the ring portions (e.g., ring portions/halves 140*a*, 140*b*) can be spaced apart from each other across opposed gaps 142, e.g., gaps aligned along the X-axis. The rest of the member forming the docking station (e.g., an elongated member or wire) bends down to define two anchors 144*a*, 144*b* on a second/lower side (e.g., ventricular anchors on the ventricular side) of the X/Y plane whose shape will be described below. Implanted, for example, in the mitral annulus, the open round or oval upper ring 140 on the atrial side and fingers-like design on the ventricular side provides compression without entangling with the chordae tendinea.

With reference to FIG. 6C, the four ends of the ring portions/halves 140*a*, 140*b* descend in approximately 180° bends 150 leading to diverging primary struts 152. Stated another way, a symmetric pair of descending bends 150 on both pairs of adjacent ends of the ring portions/halves 140*a*, 140*b* (and other portions, if included) extend vertically downward from the adjacent ends and turn approximately 180°. The primary struts 152 extend generally parallel to (or slightly angled downward) and below the adjacent portions of the ring portions/halves 140*a*, 140*b*, and each extend around a circumferential span of θ (e.g., about 45° or within a range of about 30-60°). The struts 152 then transition into curved ends 154 that lead to a secondary strut 156 that extends the width of the respective anchor 144*a*, 144*b* (e.g., a respective ventricular anchor). The curved ends 154 make approximately 180° turns. There is no short downward bridge portion included, as there is in the embodiment depicted in FIG. 1. However, the anchors/ventricular anchors 144*a*, 144*b* each define two generally rounded V-shaped projections formed by the primary struts 152, the curved ends 154, and the bridging secondary strut 156. Both arms curve within the upper ring 140 (e.g., atrial ring) and are located slightly radially inward therefrom. In some embodiments, additional anchors can be used beyond the two anchors 144*a* and 144*b* shown, e.g., three or more anchors. The anchors can be the same as or similar to any other anchors described herein, and the docking station can be implanted using the same or similar steps to those discussed above.

FIGS. 6B and 6C include exemplary dimensions on the docking station 120 which also may apply to docking station 20 or any docking station embodiments herein. An overall diameter D is shown to the outside of the member/wire that forms the docking station. The diameter D may vary depending on the particular size of the native annulus and/or the size of the prosthetic valve 80, but generally ranges between about 25-33 mm. Of course, the outward force of the expandable valve may also affect the diameter D, with a balance being desired between under- and over-expanding the docking station. Preferably the expandable valve 80 makes contact with the docking station and expands a small degree more to create the secure frictional holding force.

FIGS. 6B and 6C also show the main dimensions of the exemplary anchors/ventricular anchors 144*a*, 144*b*—the angular span θ of each curved V-shaped arm, the radially inward diversion A from the atrial ring 140, and the axial depth H to which each anchor descends below the ring 140. As mentioned the angular span θ of each curved V-shaped arm is between about 30-60°, or in absolute terms between about 10-20 mm. (That means the ventricular anchors 144*a*, 144*b* extend around between 60-120°, or about 20-40 mm.) Each anchor/ventricular anchor 144*a*, 144*b* diverts radially inward a dimension A from the first/upper ring 140 of between about 2-3 mm. Stated another way, if the diameter of the first/upper ring 140 is between about 25-33 mm, the anchors/ventricular anchors 144*a*, 144*b* together can define a diameter that is between about 19-27 mm (diameter up to 6 mm less). Each anchor/ventricular anchor 144*a*, 144*b* drops down below the first/upper ring 140 the depth H of between about 10-15 mm. And finally, the thickness of the member/wire is preferably between 0.5-1.0 mm.

Retention of the docking station is achieved via several mechanisms:

Systolic retention: a) The docking station 20, 120 retention is achieved by the anchors/ventricular anchors 44, 144 that are pressed against the annulus or surrounding tissue (e.g., pressed against the left ventricle "ceiling" and/or possibly pinching the annulus with the first/upper ring). b) The retention of the prosthetic valve 80 deployed inside the docking station 20, 120 is achieved by sandwiching the native leaflets and/or chordae between its body and the anchors/ventricular anchors 44, 144. The relative radial force between the prosthetic valve 80 and the docking station 20, 120 prevents relative movement between the prosthetic valve 80 and the docking station 20, 120 (e.g., prevents relative axial movement).

Diastolic retention: a) The same radial force between the anchors/ventricular anchors 44, 144 and the prosthetic valve 80 keeps the valve in place during diastole by having both the prosthetic valve and ring "hanging" on or trapping the native leaflets. b) Additional retention may be achieved by the prosthetic valve design for example by having an atrial body that will support the prosthetic valve during diastole by leaning on the atrial floor.

While the invention has been described with reference to particular embodiments, it will understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. For example, the features described with respect to one embodiment can be incorporated into other embodiments and the steps described with respect to one method/embodiment may be used with other methods/embodiments. Also, steps can be omitted or rearranged as desired. Therefore, it is intended that the invention not be limited to the particular embodiments disclosed herein, but that the invention will include all embodiments falling within the scope of the appended claims.

What is claimed is:

1. A mitral heart valve docking station, comprising:
   a super elastic member comprising an elongated length of rod or wire forming a continuous, closed shape defining:
   a first ring arranged around a central axis, lying in a common horizontal plane, and sized to circumscribe a mitral annulus formed by at least two ring portions lying in the common horizontal plane and the at least two ring portions are each separated at pairs of adjacent ends by gaps lying in the common horizontal plane, wherein the central axis defines upward and downward vertical directions where the horizontal plane of the first ring is located at an upper position along the central axis;

a symmetric pair of descending bends on both pairs of adjacent ends of the at least two ring portions extending downward from the adjacent ends and bending through an included angle of 180°; and a pair of V-shaped arcuate arms extending from each pair of descending bends to a position parallel to the central axis lower than the horizontal plane of the first ring with apices pointed away from each other, wherein a lower strut on each arm of each pair of arcuate arms connects to the lower strut on the other arm of that pair;

wherein the first ring forms a circle interrupted by the gaps.

2. The docking station of claim 1, wherein the arms are each curved around the central axis.

3. The docking station of claim 2, wherein the arms each have a radius of curvature around the central axis less than a radius of curvature around the central axis of the first ring.

4. The docking station of claim 3, wherein a diameter of the first ring is between 25-33 mm, and the radius of curvature of the arms is 2-3 mm less than the radius of the first ring.

5. The docking station of claim 4, wherein the arms each descend parallel to the central axis to a position lower than the horizontal plane of the first ring to a depth of between 10-15 mm.

6. The docking station of claim 1, wherein the first ring is an atrial ring and the arms are ventricular arms, and wherein each of the ventricular arms descend parallel to the central axis to a position lower than the horizontal plane of the atrial ring to a depth of between 10-15 mm.

7. The docking station of claim 1, wherein the at least two ring portions are two half rings and an angular span of each half ring is between 170-178°.

8. The docking station of claim 1, wherein the lower strut on each arm of each pair of arcuate arms connects to the lower strut on the other arm of that pair via a downwardly curved bridge portion formed to relieve resistance to bending by forming a curve that extends downward from the lower struts.

9. The docking station of claim 1, wherein the member is formed from a single length of wire having two free ends connected by a crimp.

10. The docking station of claim 1, wherein the docking station is a mitral valve docking station, the first ring is an atrial ring, and the arms are ventricular arms.

11. A mitral heart valve docking station, comprising:

an elongated member comprising an elongated length of rod or wire and defining:

two half rings arranged around a central axis, lying in a common horizontal plane, and separated at two pairs of adjacent ends by gaps lying in the common horizontal plane, the two half rings defining an incomplete ring sized to fit around a mitral annulus; and a pair of ventricular anchors each connected to a pair of adjacent ends of the half rings and axially spaced from the half rings, each of the ventricular anchors having two arms extending away from each other, and each ventricular anchor being curved around the central axis and spaced radially inward from the half rings;

wherein the incomplete ring forms a circle interrupted by the gaps.

12. The docking station of claim 11, wherein a diameter of the incomplete ring is between 25-33 mm, and the ventricular anchors have a radius of curvature around the central axis that is 2-3 mm less than the radius of the incomplete ring.

13. The docking station of claim 12, wherein the ventricular anchors are each axially spaced from the half rings a distance of between 10-15 mm.

14. The docking station of claim 11, wherein the ventricular anchors are each axially spaced from the half rings a distance of between 10-15 mm.

15. The docking station of claim 11, wherein an angular span of each half ring is between 170-178°.

16. The docking station of claim 11, wherein the gaps have a width of between 1-6 mm.

17. The docking station of claim 11, wherein the central axis defines upward and downward directions, and wherein the arms of each ventricular anchor have a rounded V-shape formed by an upper strut, a curved end defining an apex of the arm, and a lower strut, and the lower strut of each pair of arms connects to the lower strut on the other arm of that pair.

18. The docking station of claim 17, wherein the lower strut on each arm of each pair connects to the lower strut on the other arm of that pair via a downwardly curved bridge portion formed to relieve resistance to bending by forming a curve that extends downward from the lower struts.

19. The docking station of claim 11, wherein the elongated member is formed from a single length of wire having two free ends connected by a crimp.

* * * * *